(12) United States Patent
Bouvier et al.

(10) Patent No.: US 7,439,030 B2
(45) Date of Patent: Oct. 21, 2008

(54) PREPARING MEMBRANE RECEPTORS FROM EXTRACELLULAR BACULOVIRUSES

(75) Inventors: Michel Bouvier, Montréal (CA); Thomas Loisel, Montréal (CA); Stefano Marullo, Paris (FR); Pierre Boulanger, Montpellier (FR); Arthur Donny Strosberg, Paris (FR)

(73) Assignees: Valorisation-Recherche, Limited Partnership, Montreal (CA); Centre National de la Recherche Scientifique, Paris Cedex (FR)

( * ) Notice: Subject to any disclaimer, the term of this patent is extended or adjusted under 35 U.S.C. 154(b) by 0 days.

(21) Appl. No.: 11/409,998

(22) Filed: Apr. 25, 2006

(65) Prior Publication Data

US 2006/0281150 A1 Dec. 14, 2006

Related U.S. Application Data

(60) Continuation of application No. 10/732,815, filed on Dec. 11, 2003, now Pat. No. 7,078,189, which is a division of application No. 09/402,471, filed on Feb. 29, 2000, now Pat. No. 6,713,278.

(30) Foreign Application Priority Data

Apr. 11, 1997 (FR) .................................. 97 04476

(51) Int. Cl.
*G01N 33/566* (2006.01)
*C07K 14/705* (2006.01)

(52) U.S. Cl. ..................... 435/7.2; 435/7.21; 436/501

(58) Field of Classification Search ....................... None
See application file for complete search history.

(56) References Cited

FOREIGN PATENT DOCUMENTS

| WO | WO 88 07082 A | 9/1988 |
|----|---------------|--------|
| WO | WO 96 09074 A | 3/1996 |
| WO | WO 96 38575 A | 12/1996 |

OTHER PUBLICATIONS

Parker et al. Reconstitutively Active G Protein-coupled Receptors Purified from Baculovirus-infected Insect Cells. Jan. 5, 1991, J. Biol. Chem. 266(1):519-526.*
Raivio, E., et al; "Expression of the Human Interleukin-2 Receptor Gamma Chain in Insect Cells Using a Baculovirus Expression Vector"; *Scandinavian Journal of Immunology*; 41, 338-342, (1995).
Loisel, T.P., et al; "Recovery of Homogeneous and Functional $\beta_2$-adrenergic Receptors from Extracellular Baculovirus Particles"; *Nature Biotechnology*; 15(11), 1300-1304 (1997).
Parker, E.M., et al; "Reconstitutively Active G Protein-coupled Receptors Purified from Baculovirus-infected Insect Cells"; *Journal of Biological Chemistry*; vol. 266, No. 1, pp. 519-527, Jan. 5, 1991.

\* cited by examiner

*Primary Examiner*—John D Ulm
(74) *Attorney, Agent, or Firm*—Nixon & Vanderhye

(57) ABSTRACT

The present invention describes a method for producing membrane receptors based on a baculovirus/insect cell system. The invention further includes the receptors produced by the method described herein, a model for studying the properties of these membrane receptors and an assay to screen molecules that are active on these membrane receptors.

24 Claims, 3 Drawing Sheets

PREPARING MEMBRANE RECEPTORS FROM EXTRACELLULAR BACULOVIRUSES

CROSS-REFERENCE TO RELATED APPLICATIONS

This application is a continuation of application Ser. No. 10/732,815, filed Dec. 11, 2003, now U.S. Pat. No. 7,078,189 which is a divisional of application Ser. No. 09/402,471, filed Feb. 29, 2000, now U.S. Pat. No. 6,713,278 the entire content of which is hereby incorporated by reference in this application.

FIELD OF THE INVENTION

The invention relates to the production of membrane receptors in a baculovirus/insect cell system.

BACKGROUND OF THE INVENTION

Over the past few years, heterologous expression systems have often been used to study the expression as well as the pharmacological and biochemical characteristics of membrane receptors.

Although a significant expression can be obtained in some expression systems in mammalian cells, there have been problems, in particular in the case of some types of receptors such as the G-protein-coupled receptors.

The G-protein-coupled receptors belong to the superfamily of receptors with seven transmembrane domains. They comprise, for example, the adrenergic or muscarinic receptors, and all have the same structure which is made up of a polypeptide chain comprising seven hydrophobic domains which cross the membrane lipid bilayer.

When it is desired to express these receptors in mammalian cell systems, a relatively low density of receptors expressed by the said cells, rarely exceeding a few picomoles of receptor per milligram of membrane protein, is generally obtained. Although these levels of expression are sufficient for a functional and pharmacological characterization, they clearly limit the type of biochemical, biophysical and structural studies which can be carried out. A fortiori, this expression system cannot be used for the production of receptors in a large quantity, for example for their therapeutic use.

To increase the quantity of receptors obtained, various teams have sought to produce them in a baculovirus/insect cell system; in many cases, baculoviruses expressing G-protein-coupled receptors have been able to produce these recombinant receptors in cells of the *Spodoptera frugiperda* Sf9 or Sf21 lines, up to levels reaching 30 to 100 picomoles per milligram of membrane protein. These systems have made it possible to make significant progress in the study of the palmitoylation of receptors and also to study the effects produced by various agonists and antagonists, or to carry out the reconstitution of artificial receptors.

However, the baculovirus/insect cell system has the major disadvantage of expressing a high proportion of inactive receptors. The receptors, which are recovered in the membrane fraction of the cells infected with the baculoviruses are in an immature and incompletely glycosylated form. This probably results from a saturation of the normal post-translational maturation pathway, which brings about the retention of immature receptors in the membranes of the endoplasmic reticulum or in the Golgi apparatus. To obtain functional receptors, it is necessary in this case to include a purification step based on the biological activity of the receptor (for example an affinity chromatography step).

It would therefore be necessary to develop a system which makes it possible to easily separate the plasma membrane comprising the mature receptors from the other membrane fractions such as the endoplasmic reticulum or the membranes of the Golgi apparatus which comprise the biologically inactive, immature receptor.

SUMMARY OF THE INVENTION

It has recently been shown that the infection of Sf9 cells with a baculovirus encoding the HIV1 Gag gene (Pr55 Gag) brings about the budding of particles carrying the Gag protein (Gag particles) which are released into the extracellular medium. It has been suggested that these Gag particles carry with them, during their budding, the plasma membrane and the proteins associated with it.

The inventors have formulated the hypothesis that the coexpression, in a baculovirus/insect cell system, of a G-protein-coupled receptor and of Pr55 Gag can promote the release of the Gag particles expressing only the mature receptors which are correctly inserted into the plasma membrane. To test this hypothesis, the inventors infected Sf9 cells with baculoviruses encoding the human adrenergic receptor β2AR and the Pr55 Gag protein. Surprisingly, they then observed that the β2AR receptor is almost completely absent from the Gag particles, but is, one the other hand, present at a high density in extracellular baculovirus particles. In addition, the receptors expressed in these extracellular baculoviruses are correctly glycosylated and normally active.

The present invention relates to the use of these extracellular baculoviruses for the production of preparations of a membrane receptor.

The subject of the present invention is a method of producing a recombinant membrane receptor in a baculovirus/insect cell system, from a culture of insect cells infected with a recombinant baculovirus expressing the gene encoding the said membrane receptor, which method is characterized in that the said membrane receptor is obtained from extracellular baculoviruses produced by the said infected cells.

According to a preferred embodiment of the present invention, the said receptor belongs to the superfamily of receptors with seven transmembrane domains; this is for example a receptor of the family of G-protein-coupled receptors.

Recombinant baculoviruses expressing the gene encoding the membrane receptor which it is desired to produce are obtained by cloning the said gene under transcriptional control of an appropriate promoter of the said baculovirus, according to methods well known per se to persons skilled in the art.

Any strong baculovirus promoter which can be used for the expression of heterologous genes, such as for example the polyhedrin promoter (polh) or that of the P10 protein, may be used for the production of a recombinant baculovirus which can be used within the framework of the present invention.

According to a preferred embodiment of the method in accordance with the invention, it comprises a step during which the extracellular baculoviruses produced by the said infected cells are lysed; advantageously, it also comprises a step during which the lysate obtained at the end of the preceding step is fractionated, and the fraction comprising the said membrane receptor is recovered.

The purified preparations and the lysates of extracellular baculoviruses, as well as their fractions comprising the membrane receptor, which are capable of being obtained by the methods defined above constitute membrane preparations which also form part of the subject of the present invention. These preparations consist of active and fully mature receptors, unlike the membrane receptor preparations obtained in the prior art from the plasma membranes of infected cells, which comprise a high proportion of inactive receptors, and which can only be used after an additional step of purification on the basis of the activity of the relevant receptors, for example after affinity chromatography.

By contrast, the membrane receptor preparations in accordance with the invention are characterized in that, prior to any purification carried out on the basis of the activity of the relevant receptor, at least 90%, and preferably at least 95%, of the said receptor is in an active form.

Preparations, in accordance with the invention, of a membrane receptor may be used to prepare the said receptor in a purified form, with a much better yield than that which could be achieved from membrane receptor preparations obtained in the prior art from the plasma membranes of infected cells.

The membrane receptor preparations in accordance with the invention, as well as the extracellular baculoviruses obtained using the method in accordance with the invention, may also be used directly, for example as a system for studying the properties of membrane receptors, as a system for screening molecules which are active on these membrane receptors, or alternatively for studying their post-translational modifications such as phosphorylation or palmitoylation.

DETAILED DESCRIPTION OF THE INVENTION

Figure 1:
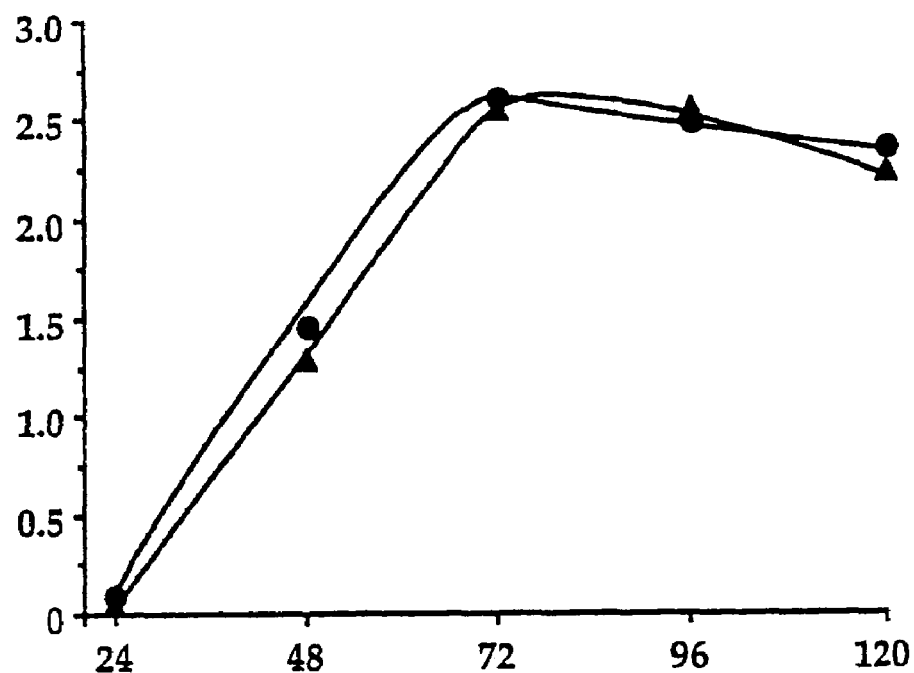
FIG. 1: β2AR activity in extracellular recombinant baculoviruses versus hours.

The present invention will be understood more clearly with the aid of the additional description which follows, which refers to exemplary embodiments of the method in accordance with the invention for the preparation of membrane receptors.

EXAMPLE 1

Preparation of Recombinant Baculoviruses Expressing a G-Protein-Coupled Receptor A recombinant baculovirus expressing β2AR is obtained by cloning a DNA sequence consisting of the cDNA for β2AR in fusion with the c-myc epitope, obtained as described by MOUILLAC et al. [J. Biol. Chem., 267, 21733-21737 (1992)], at the NheI site of the transfection/recombination vector pJVNheI (marketed by the company INVITROGEN). This vector was transfected with the linearized genome of a baculovirus AcMNPV (sold by the company INVITROGEN) into Sf9 cells; the recombinant baculovirus obtained in this manner is called c-myc-β2AR.

In the same manner, the sequence encoding the muscarinic receptor M1 and the sequence encoding the dopaminergic receptor D1 [respectively described by ALLARD et al. Nucleic Acid Research, 15, p 10604, (1987) and by DEARRY et al., Nature, 347, p 72, (1990)] were cloned in order to obtain the recombinant baculoviruses (respectively called M1-R and D1-R) expressing these receptors.

a) Culture and infection of the cells, and harvesting of the extracellular baculoviruses:

Sf9 cells are cultured at 27° C. in culture flasks in a 100 ml suspension (BELLCO GLASS) in supplemented GRACE medium (GIBCO) containing 10% foetal calf serum (FCS), and 0.001% pluronic acid. 60 ml of suspension of cells ($2\times10^6$/ml) are infected with the recombinant baculovirus expressing β2AR, D1 or M1, at a multiplicity of infection varying between 2 and 5.

The cells are harvested by centrifugation at 500×g for 5 min at 4° C.

The viral particles are isolated after harvesting the cells, by centrifugation of the culture supernatant at 45,000×g for 20 min at 4° C. The pellets obtained are resuspended at 4° C. in a volume of phosphate-buffered saline (PBS) equal to 1/10th of the volume of the initial culture, and centrifugated at 500×g for 5 minutes at 4° C.; the supernatant for this centrifugation at 500×g is again centrifuged at 45,000×g for 20 min at 4° C.

b) Purification of the baculovirus particles on a sucrose gradient.

The pellet of viral particles which is obtained from 100 ml of cultures of Sf9 cells infected with the recombinant baculovirus expressing β2AR, M1 or D1 is resuspended in 1.2 ml of TE solution (10 mM Tris-HCl, 1 mM EDTA, pH 7.4), in the presence of protease inhibitors).

The suspension is deposited at the top of a tube containing a linear gradient (25%-56%) of sucrose in TE solution. The tubes are centrifuged at 100,000×g for 90 minutes. The gradient is collected from the top to the bottom of the tube, in 20 fractions. The first fraction has a volume of 1.4 ml, and the other 19 are 500 μl.

EXAMPLE 2

Demonstration of the β2AR Activity in the Extracellular Recombinant Baculoviruses The Sf9 cells infected with the recombinant baculovirus expressing β2AR are cultured, and the baculoviruses are harvested as described in Example 1 a), 24 hours, 48 hours, 72 hours, 96 hours and 120 hours after the infection.

The activity of the β2AR receptors is evaluated by measurements of saturation and of competitive binding which are carried out as described by BOUVIER et al. [Mol. Pharmacol. 33:133-139 (1982)] using [$^{125}I$] iodocyanopindolol ([$^{125}I$] ICYP) as labelled ligand.

The pellets of viral particles which are obtained are resuspended at 4° C. in the buffer which will be used for the reaction. Aliquots of this suspension of viral particles, corresponding to 0.2 to 1 μg of proteins are mixed with 5 to 350 pM of radioligand [$^{125}I$] ICYP in a final volume of 500 μl. The non-specific binding is evaluated using 10 μM of alprenolol.

Under these conditions, the β2AR activity is detected in the cell culture supernatants from 48 hours after the infection, reaches its maximum 72 hours after the infection, and remains constant up to 120 hours after the infection.

These results are illustrated in FIG. 1.

This figure also shows the results obtained, under the same experimental conditions, on culture supernatants of cells infected both with the recombinant baculovirus c-myc-β2AR, and a recombinant baculovirus expressing the HIV Gag protein (●=β2AR; ◆=β2AR+Gag). It is observed that, contrary to what was initially expected, the presence of the Gag protein does not increase the quantity of β2AR in the culture supernatants.

It is also observed that the β2AR activity detected in the supernatants does not come from the cell lysis, since this activity appears 48 hours after the infection; that is to say at a time where the majority of the infected cells are still viable, and does not increase between 72 and 120 hours after the infection, in spite of the substantial cell lysis which occurs at this time.

The nature of the particles in the supernatant carrying the β2AR activity was checked by electron microscopy after labelling these particles with the aid of an antibody directed against the c-myc antigen, or an antibody directed against the β2AR receptor. It was thus observed that the particles recognized by either of these antibodies are 15×100 nm rods, which corresponds to extracellular baculoviruses.

In the case of the co-infection with a baculovirus expressing the Gag protein, the presence of particles exhibiting the morphology of the Gag particles, and which are recognized by an anti-Gag antibody, is observed, in addition, in the supernatant; however, unlike the extracellular baculoviruses, these Gag particles are only very weakly recognized by the anti-c-myc and antiβ2AR antibodies.

The presence of the β2AR receptor was also verified in the preparations of recombinant baculovirus c-myc-β2AR which are purified on a sucrose gradient, as described in Example 1 b) above.

The β2AR activity was determined according to the protocol described in Example 2 above, on various fractions of the gradient.

In parallel, the detection of the vp80, gp67 and vp39 antigens of the baculovirus AcNMPV, using a polyclonal antibody directed against these antigens, was carried out on the same fractions. The results obtained show that the β2AR activity cosediments with the viral particles.

All the results obtained above show that not only are molecules of the receptor expressed in the recombinant extracellular baculoviruses, but also that they are active molecules.

The quantification of the β2AR activity in the recombinant extracellular baculovirus preparations purified on a sucrose gradient makes it possible to evaluate the density of the active receptor at about 25 pmol/mg of total proteins.

EXAMPLE 3

Comparison of the Forms of the β2AR Receptor which are Present in Cell Membrane Preparations and in the Extracellular Baculoviruses Sf9 cells infected with the recombinant baculovirus c-myc-β2AR are harvested 72 hours after the infection. The extracellular baculoviruses c-myc-β2AR are harvested from the culture supernatant of these cells, and the viral particles are purified as described in Example 1 b).

The membranes of the Sf9 cells are prepared as follows: the cells are centrifuged at 500×g for 5 minutes at 4° C., rinsed once with PBS buffer at 4° C., and resuspended in lysis buffer (20 mM Tris-HCl, 5 mM EDTA, pH 7.4 containing 5 µg/ml leupeptin, 5 µg/ml of trypsin inhibitor and 10 µg/ml of benzamidine) at 4° C. The cells are then lysed by sonication, the lysates are centrifuged for 5 min at 500×g at 4° C. and the supernatants centrifuged at 45,000×g for 20 min at 4° C. The pellets are resuspended at 4° C. in reaction buffer (75 mM Tris-HCl (pH 7.4), 12.5 mM magnesium chloride, 2 mM EDTA), in the presence of protease inhibitors.

6 mg of the cell membrane preparation or of the purified baculovirus preparation are added to 5 ml of solubilization buffer (10 mM Tris-HCl, 100 mM NaCl, 2 mM EDTA, pH 7.4, 0.3% n-dodecyl maltoside (BOEHRINGER MANNHEIM) in the presence of protease inhibitors. The solubilization is carried out for 90 min at 4° C.

The solubilized receptors are purified by affinity chromatography as described below. The ALPRENOLOL-SEPHAROSE affinity matrix is synthesized according to the method of BENOVIC et al. [J. Biol. Chem., 262:9026-9032, (1987)]. This matrix is used to purify c-myc-β2AR according to the protocol described by MOUILLAC et al. [J. Biol. Chem., 267:21733-21737, (1992)]. All the buffers comprise n-dodecyl maltoside (0.05%).

Figure 2:
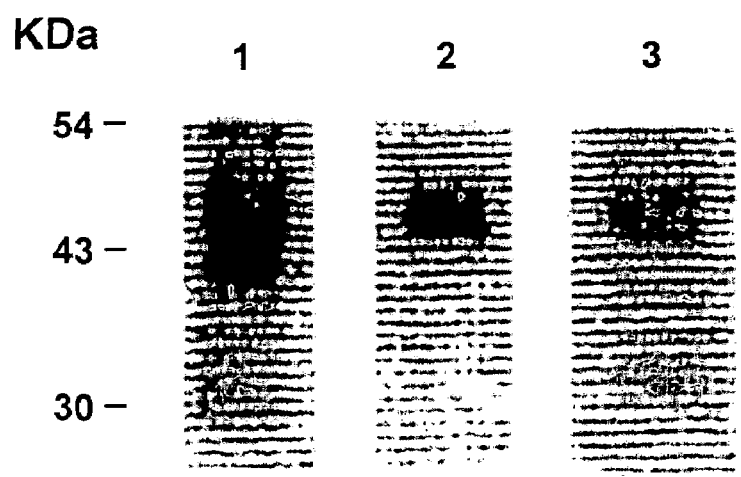
FIG. 2: Comparison of the forms of β2AR receptor present in cell membrane preparations and in extracellular baculoviruses.

The preparations obtained after affinity chromatography are concentrated using CENTRIPREP and CENTRICON cartridges (AMICON) and the quantity of c-myc-β2AR in each sample is determined using [$^{125}$I]-iodocyanopindolol ([$^{125}$I] ICYP) as described by MOUILLAC et al. [J. Biol. Chem., 267:21733-21737, (1992)]. The preparations of viral particles, of membranes or of β2AR purified by affinity chromatography are subjected to a polyacrylamide gel electrophoresis in the presence of SDS (SDS-PAGE), under nonreducing conditions, on 10% gel plates. The proteins separated on the gels are transferred onto nitrocellulose and revealed with an anti-c-myc mouse monoclonal antibody, and a second anti-mouse antibody coupled to alkaline phosphatase or to horseradish peroxidase. The results are illustrated by FIG. 2.

The Western blotting of the cell membrane preparation (FIG. 2, lane 1) shows the presence of several immunoreactive bands, between 40 and 50 kDa.

The Western blotting of the preparations of β2AR purified by affinity chromatography (FIG. 2, lane 2) shows a single and broad immunoreactive band, between 46 and 50 kDa, which represents the biologically active mature form of the β2AR receptor.

The Western blotting of the purified extracellular baculovirus preparation (FIG. 2, lane 3) also shows the presence of a single and broad immunoreactive band between 46 and 50 kDa.

These results show that the β2AR receptor molecules present in the extracellular baculoviruses represent only the biologically active form, unlike the β2AR receptor molecules present in the cell membrane preparations, which represent a mixture of active and inactive forms.

EXAMPLE 4

Pharmacological Properties of Various Receptors Expressed in the Extracellular Baculoviruses Preparations of extracellular baculoviruses expressing the β2AR, M1 or D1 receptors are obtained as described in Example 1 above.

The binding of each of the receptors to the ligand is evaluated as described in Example 2 above.

The competitive binding trials in the presence of agonists are carried out using 70 pM of [$^{125}$I] ICYP as radioligand. The concentration of the non-labelled ligand varies from $10^{-4}$ to $10^{-12}$ M.

The saturation assays of the M1-muscarinic (M1-R) and D1-dopaminergic (D1-R) receptors expressed in the viral particles are carried out using 1-100 nM [3H] pirenzepine (NEN, DUPONT) and 0.02-3 nM [$^{125}$I]—R(+) SCH-23390 (NEN, DUPONT) with 5-10 µg or 1-2 µg of protein for M1-R and D1-R respectively. To evaluate non-specific binding, 1 µM atropine (RBI) is added to the reaction mixture for M1-R, and 10 µM haloperidol (RBI) for D1-R.

The results of these experiments are illustrated by Table I below.

TABLE I

| Receptor | Ligand | Kd pM | BMax pmol/mg of protein | Ki µm |
|---|---|---|---|---|
| β2AR | [$^{125}$I] ICYP | 49.4 ± 11.5 | | |
| | Epinephrine | | | 8.98 ± 4.02 |
| | Arterenol | | | 3.27 ± 0.38 |
| M1 | [$^3$H] - Pirenzepine | 1360 ± 670 | 5.56 ± 0.46 | |
| D1 | [$^{125}$I] - SCH23390 | 118 ± 63 | 5.21 ± 0.84 | |

These results show that various receptors of the G-protein-coupled receptor family are expressed in an active form in extracellular baculoviruses.

EXAMPLE 5

Palmitoylation of the β2AR Receptor Expressed in Extracellular Baculoviruses

The viral particles expressing c-myc-β2AR are prepared as described in Example 1 above, and the pellet resuspended in PBS. 1 mCi of [$^3$H] palmitate dissolved in dimethyl sulphoxide is added to the viral particles. The reaction is carried out for defined periods in the presence or the absence of 1 µM (final concentration) of isoproterenol.

Figure 3:
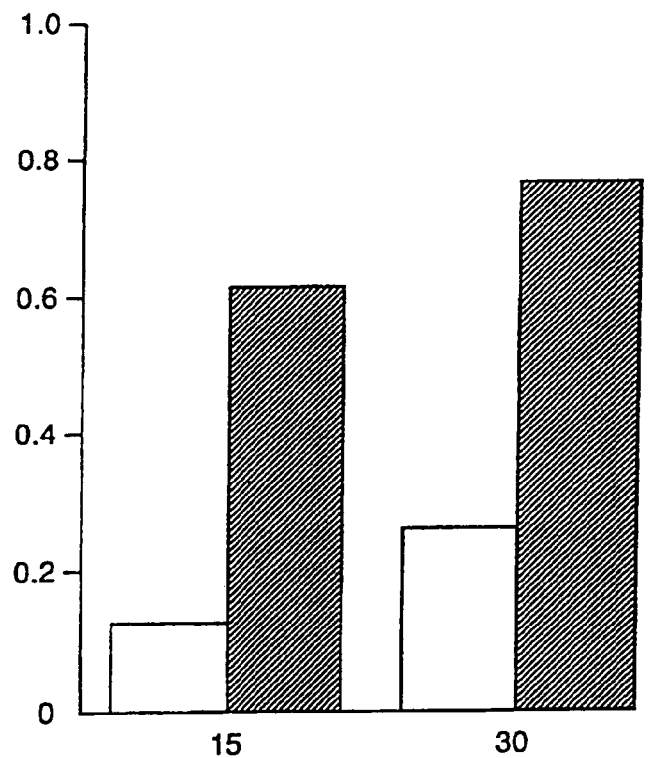
FIG. 3: Palmitoylation of β2AR receptors expressed in extracellular baculoviruses. Clear bars: incorporation in the absence of isoproterenol; Etched bars: incorporation in the presence of isoproterenol.

The results are illustrated by FIG. 3: Legend to FIG. 3:
☐: incorporation in the absence of isoproterenol;
▨: incorporation in the presence of isoproterenol.

EXAMPLE 6

Comparison of the Forms of the β2AR Receptor

The viral particles expressing c-myc-β2AR are prepared as described in Example 1 above, and the pellet resuspended in a buffer (100 mM Tris-HC1, 10 mM MgCl$_2$, pH 7.4 and protease inhibitors). 1 volume of extracellular baculoviruses and 1 volume of phosphorylation mixture (2.3 µCi/µl of [γ$^{32}$P] ATP, 10 mM Tris-HCl, 2 mM MgCl$_2$, pH 7.4, 25 mM phosphoenol pyruvate, 0.3 mM GTP, 1 mM ATP, 4 U/ml of pyruvate kinase and 20 U/ml of myokinase) are mixed. The reaction is carried out for 25 min at 30° C. At the end of the reaction, the incorporation of $^{32}$P is measured in the absence of activator (control) or in the presence of 1 µM of isoproterenol, or of 100 µM of dibutyril cyclic AMP, or of 100 µM of forskolin. The results are illustrated by FIG. 4.

Figure 4:
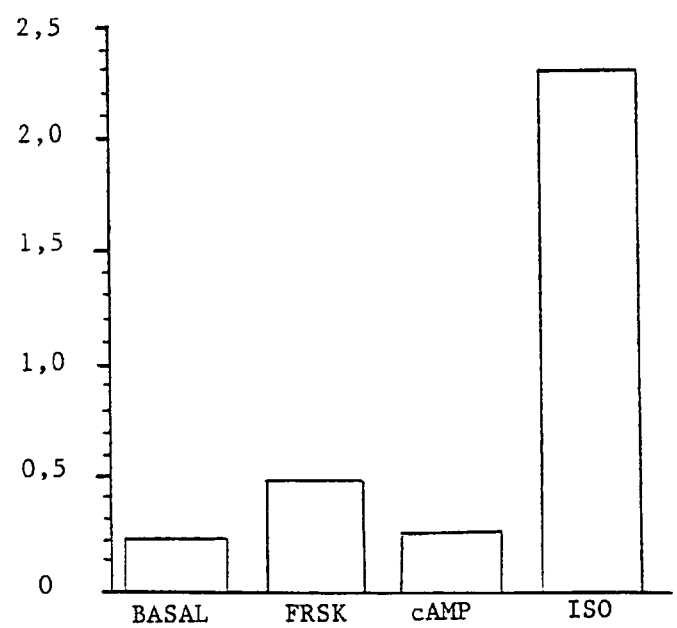
FIG. 4: Comparison of forms of the β2AR receptor. On the y-axis: relative incorporation of $^{32}P$ (arbitrary units). On the x-axis: BASAL=control; FRSK=incorporation in the presence of forskolin; cAMP=incorporation in the presence of dibutyril cyclic AMP; and ISO=incorporation in the presence of isoproterenol.

Legend to FIG. 4:
On the y-axis: relative incorporation of $^{32}$P (arbitrary units)
On the x-axis:

| BASAL | control |
| FRSK | incorporation in the presence of forskolin |
| cAMP | incorporation in the presence of dibutyril cyclic AMP |
| ISO | incorporation in the presence of isoproterenol |

EXAMPLE 7

Functionality of the β2AR Receptor Expressed in Extracellular Baculoviruses

The viral particles expressing c-myc-β2AR are prepared as described in Example 1 above, and the pellet resuspended in a buffer (75 mM Tris-HCl, 12.5 mM MgCl$_2$, 2 mM EDTA, pH 7.4 and protease inhibitors). 20 µl of extracellular baculovirus suspension are mixed with 30 µl of reaction medium containing 0.2 mM ATP, 0.090. mM GTP, 0.20 mM cAMP, 0.20 mM isobutyl-methylxanthine, 1 µCi [γ$^{32}$P] ATP, 5 mM phosphoenol pyruvate, 0.3 U of pyruvate kinase and 2 U of myokinase. After incubating for 30 min at 37° C., the reactions are stopped by the addition of 1 ml of stop solution (0.4 mM ATP, 0.3 mM cyclic AMP and 25,000 cpm of tritiated cyclic AMP). The activity was determined in the absence of activator (control) or in the presence of one of the following activators: 1 µM of isoproterenol, 10 µM NaF or 100 µM of forskolin. The results are expressed in picomoles of cyclic AMP produced per minute and per milligram of protein. These results are illustrated by FIG. 5.

Figure 5:
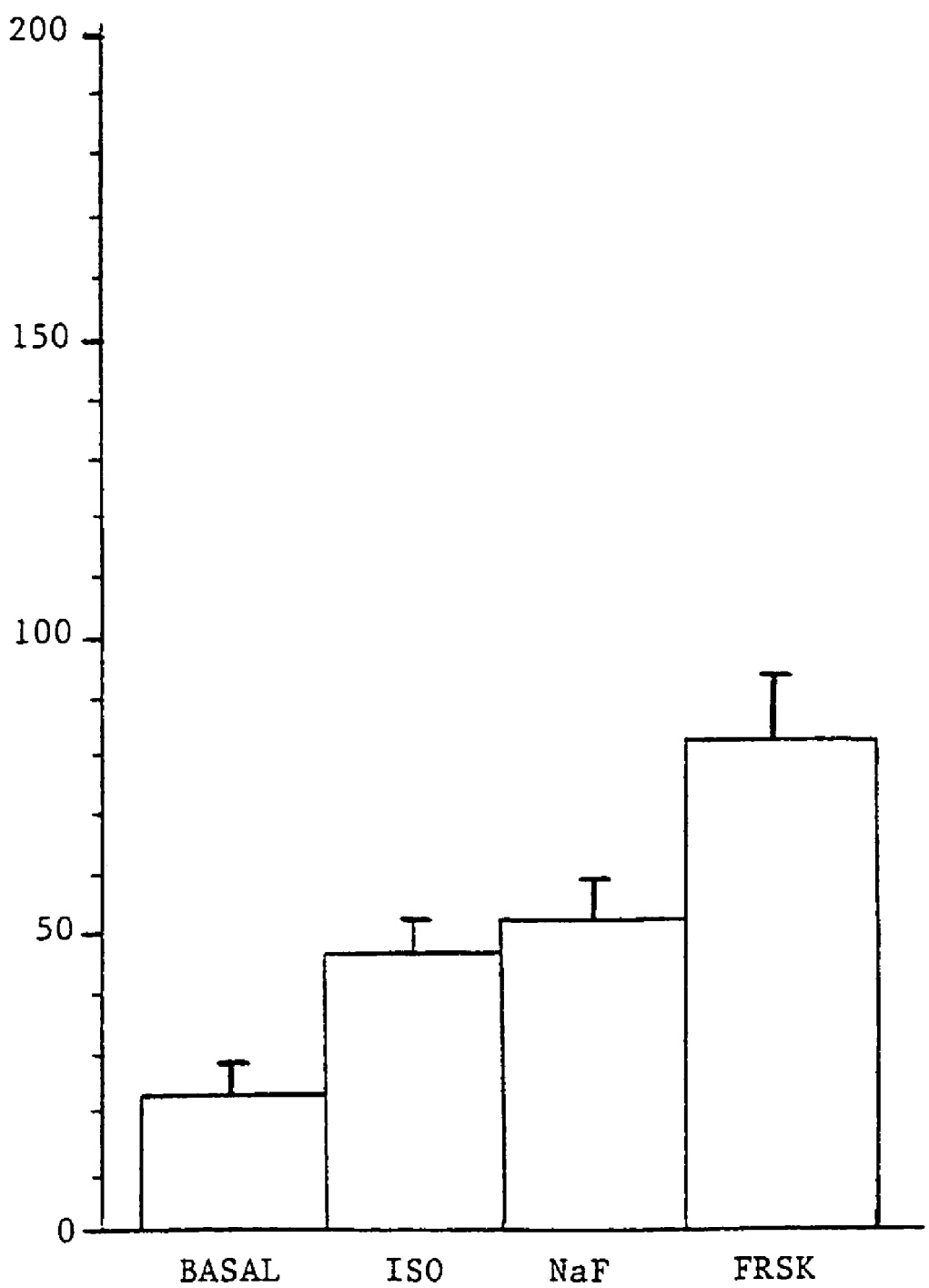
FIG. 5: Functionality of the β2AR receptor expressed in extracellular baculoviruses. On the y-axis: adenyl cyclase activity (in picomoles of cyclic AMP/min/mg of protein). On the x-axis: BASAL=control; FRSK=incorporation in the presence of forskolin; NaF=incorporation in the presence of NaF; and ISO=incorporation in the presence of isoproterenol.

Legend to FIG. 5:
On the y-axis: adenyl cyclase activity (in picomoles of cyclic AMP/min/mg of protein)
On the x-axis:

| BASAL | control |
| FRSK | incorporation in the presence of forskolin |
| NaF | incorporation in the presence of NaF |
| ISO | incorporation in the presence of isoproterenol |

These results show that the β2AR receptor present in the extracellular baculoviruses is in an environment which reproduces the natural membrane environment, and that the extracellular baculovirus preparations can therefore be used in all membrane receptor applications where a reproduction of this environment is desirable.

The invention claimed is:

1. A method of determining whether a membrane receptor present in recombinant extracellular baculoviruses is active, the method comprising:
   providing recombinant extracellular baculoviruses in which the membrane receptor is present;
   contacting the extracellular baculoviruses with a ligand to the membrane receptor; and
   determining whether binding of the ligand to the receptor occurs, wherein said binding is an indication that the receptor is active.

2. A method as defined in claim 1, wherein said receptor is a G-protein-coupled receptor.

3. A method as defined in claim 2, wherein said G-protein-coupled receptor is β2AR, M1-muscarinic receptor (M1-R) or D1-dopaminergic receptor (D1-R).

4. A method as described in claim 3, wherein said ligand is [$^{125}$I]ICYP, [3H]pirenzepine or [$^{125}$I]-R(+)SCH23390.

5. A method of determining whether a membrane receptor from isolated membranes is in active form, wherein said membrane receptor is produced by infecting a culture of insect cells with recombinant baculoviruses encoding the gene for said membrane receptor and said membrane receptor is harvested from extracellular baculoviruses generated by said insect cells, the method comprising:
 contacting the receptor with a ligand; and
 determining whether binding of the ligand to the receptor occurs, wherein said binding is an indication that the receptor is active.

6. A method as defined in claim 5, wherein said receptor is a G-protein-coupled receptor.

7. A method as defined in claim 6, wherein said G-protein-coupled receptor is β2AR, M1-muscarinic receptor (M1-R) or D1-dopaminergic receptor (D1-R).

8. A method as described in claim 7, wherein said ligand is [$^{125}$I]ICYP, [3H]pirenzepine or [$^{125}$I]-R(+)SCH23390.

9. A method of screening for molecules which are active on a membrane receptor present in recombinant extracellular baculoviruses, the method comprising:
 providing recombinant extracellular baculoviruses in which the membrane receptor is present;
 contacting the extracellular baculoviruses with a test molecule and a ligand to the membrane receptor; and
 determining whether binding of the ligand is decreased in the presence of the test molecule, wherein a decrease in said binding is an indication that the test molecule competes with the ligand for the receptor.

10. A method as defined in claim 9, wherein said receptor is a G-protein-coupled receptor.

11. A method as defined in claim 10, wherein said G-protein-coupled receptor is β2AR, M1-muscarinic receptor (M1-R) or D1-dopaminergic receptor (D1-R).

12. A method as described in claim 11, wherein said ligand is [$^{125}$I]ICYP, [3H]pirenzepine or [$^{125}$I]-R(+)SCH23390.

13. A method of screening for molecules which are active on a membrane receptor from isolated membranes, wherein said membrane receptor is produced by infecting a culture of insect cells with recombinant baculoviruses encoding the gene for said membrane receptor and said membrane receptor is harvested from extracellular baculoviruses generated by said insect cells, the method comprising:
 contacting the receptor with a test molecule and a ligand; and
 determining whether binding of the ligand is decreased in the presence of the test molecule, wherein a decrease in said binding is an indication that the test molecule competes with the ligand for the receptor.

14. A method as defined in claim 13, wherein said receptor is a G-protein-coupled receptor.

15. A method as defined in claim 14, wherein said G-protein-coupled receptor is β2AR, M1-muscarinic receptor (M1-R) or D1-dopaminergic receptor (D1-R).

16. A method as described in claim 15, wherein said ligand is [$^{125}$I]ICYP, [3H]pirenzepine or [$^{125}$I]-R(+)SCH23390.

17. A method of determining whether two or more membrane receptors are present in recombinant extracellular baculoviruses in active form, the method comprising:
 providing recombinant extracellular baculoviruses in which two or more membrane receptors are present;
 contacting the extracellular baculoviruses with a ligand specific to each membrane receptor; and
 determining whether binding of each ligand to its receptor occurs, wherein said binding is an indication that the receptor is active.

18. A method as defined in claim 17, wherein said receptors are G-protein-coupled receptors.

19. A method as defined in claim 18, wherein said G-protein-coupled receptors include at least two of β2AR, M1-muscarinic receptor (M1-R) and D1-dopaminergic receptor (D1-R).

20. A method as described in claim 17, wherein said receptors and ligands are chosen from the following: β2AR and [$^{125}$I]ICYP, M1-muscarinic receptor (M1-R) and [3H]pirenzepine, and D1-dopaminergic receptor (D1-R) and [$^{125}$I]-R(+)SCH23390.

21. A method of determining whether two or more membrane receptors from isolated membranes derived from recombinant extracellular baculoviruses are in active form, the method comprising:
 contacting the membrane receptors with ligands known to be specific to each one of the membrane receptors; and
 determining whether binding of the ligands to their respective membrane receptors occurs, wherein said binding is an indication that the membrane receptors are active.

22. A method as defined in claim 21, wherein said receptors are G-protein-coupled receptors.

23. A method as defined in claim 22, wherein said G-protein-coupled receptors include at least two of β2AR, M1-muscarinic receptor (M1-R) and D1-dopaminergic receptor (D1-R).

24. A method as described in claim 23, wherein said receptors and ligands are chosen from the following: β2AR and [$^{125}$I]ICYP, M1-muscarinic receptor (M1-R) and [3H]pirenzepine, and D1-dopaminergic receptor (D1-R) and [$^{125}$I]-R(+)SCH23390.

* * * * *